United States Patent
Swanson

(10) Patent No.: US 9,565,718 B2
(45) Date of Patent: Feb. 7, 2017

(54) SYSTEM AND METHOD FOR DETECTING AND TRANSMITTING MEDICAL DEVICE ALARM WITH A SMARTPHONE APPLICATION

(71) Applicant: Tandem Diabetes Care, Inc., San Diego, CA (US)

(72) Inventor: Vance Swanson, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 0 days.

(21) Appl. No.: 14/482,521

(22) Filed: Sep. 10, 2014

(65) Prior Publication Data
US 2015/0072613 A1    Mar. 12, 2015

Related U.S. Application Data

(60) Provisional application No. 61/875,979, filed on Sep. 10, 2013.

(51) Int. Cl.
| | |
|---|---|
| H04B 7/15 | (2006.01) |
| H04W 88/04 | (2009.01) |
| G06F 19/00 | (2011.01) |
| H04L 29/08 | (2006.01) |

(52) U.S. Cl.
CPC .......... *H04W 88/04* (2013.01); *G06F 19/3418* (2013.01); *G06F 19/345* (2013.01); *H04L 67/125* (2013.01); *H04L 67/2819* (2013.01)

(58) Field of Classification Search
None
See application file for complete search history.

(56) References Cited

U.S. PATENT DOCUMENTS

| | | |
|---|---|---|
| 5,590,648 A | 1/1997 | Mitchell et al. |
| 5,788,669 A | 8/1998 | Peterson |
| 6,551,276 B1 | 4/2003 | Mann et al. |
| 6,553,244 B2 | 4/2003 | Lesho et al. |
| 6,554,798 B1 | 4/2003 | Mann et al. |
| 6,561,978 B1 | 5/2003 | Conn et al. |
| 6,641,533 B2 | 11/2003 | Causey, III et al. |
| 6,740,059 B2 | 5/2004 | Flaherty |
| 6,780,156 B2 | 8/2004 | Haueter et al. |
| 6,852,104 B2 | 2/2005 | Blomquist |
| 6,872,200 B2 | 3/2005 | Mann et al. |
| 6,936,029 B2 | 8/2005 | Mann et al. |
| 6,979,326 B2 | 12/2005 | Mann et al. |
| 6,997,920 B2 | 2/2006 | Mann et al. |
| 7,024,236 B2 | 4/2006 | Ford et al. |
| 7,025,743 B2 | 4/2006 | Mann et al. |

(Continued)

*Primary Examiner* — Mohammed Rachedine
(74) *Attorney, Agent, or Firm* — Patterson Thuente Pedersen, P.A.

(57) ABSTRACT

A system and method provide for relaying a medical device alarm to a remote location without having a device electrically interconnected with the medical device. The system includes a relay device having software that can store specific alarm patterns or sequences for one or more alarms for a medical device. The relay device can then detect one or more of an audible, visual or tactile alarm from the medical device through corresponding devices or sensors in the relay device. Upon detection of an alarm, the relay device can transmit information pertaining to the alarm to a remote device to notify a user of the remote device of the medical device alarm.

20 Claims, 5 Drawing Sheets

(56) References Cited

U.S. PATENT DOCUMENTS

| | | |
|---|---|---|
| 7,029,455 B2 | 4/2006 | Flaherty |
| 7,109,878 B2 | 9/2006 | Mann et al. |
| 7,137,964 B2 | 11/2006 | Flaherty |
| 7,181,505 B2 | 2/2007 | Haller et al. |
| 7,278,983 B2 | 10/2007 | Ireland et al. |
| 7,497,827 B2 | 3/2009 | Brister et al. |
| 7,547,281 B2 | 6/2009 | Hayes et al. |
| 7,668,731 B2 | 2/2010 | Martucci et al. |
| 7,704,226 B2 | 4/2010 | Mueller, Jr. et al. |
| 7,711,402 B2 | 5/2010 | Shults et al. |
| 7,726,955 B2 | 6/2010 | Ryser et al. |
| 7,801,596 B2 | 9/2010 | Fischell et al. |
| 7,815,602 B2 | 10/2010 | Mann et al. |
| 7,819,843 B2 | 10/2010 | Mann et al. |
| 7,860,583 B2 | 12/2010 | Condurso et al. |
| 7,901,394 B2 | 3/2011 | Ireland et al. |
| 7,935,104 B2 | 5/2011 | Yodfat et al. |
| 7,942,844 B2 | 5/2011 | Moberg et al. |
| 7,976,508 B2 | 7/2011 | Hoag |
| 8,002,700 B2 | 8/2011 | Ferek-Petric et al. |
| 8,005,540 B2 | 8/2011 | Zhang et al. |
| 8,057,679 B2 | 11/2011 | Yu et al. |
| 8,062,513 B2 | 11/2011 | Yu et al. |
| 8,118,770 B2 | 2/2012 | Galley et al. |
| 8,149,131 B2 | 4/2012 | Blomquist |
| 8,177,739 B2 | 5/2012 | Cartledge et al. |
| 8,206,350 B2 | 6/2012 | Mann et al. |
| 8,250,483 B2 | 8/2012 | Blomquist |
| 8,269,634 B2 | 9/2012 | Fischell et al. |
| 8,287,495 B2 | 10/2012 | Michaud et al. |
| 8,311,749 B2 | 11/2012 | Brauker et al. |
| 8,323,188 B2 | 12/2012 | Tran |
| 8,340,792 B2 | 12/2012 | Condurso et al. |
| 8,344,847 B2 | 1/2013 | Moberg et al. |
| 8,346,399 B2 | 1/2013 | Blomquist |
| 8,348,885 B2 | 1/2013 | Moberg et al. |
| 8,408,421 B2 | 4/2013 | DiPerna |
| 8,414,563 B2 | 4/2013 | Kamen et al. |
| 8,435,206 B2 | 5/2013 | Evans et al. |
| 8,444,595 B2 | 5/2013 | Brukalo et al. |
| 8,448,824 B2 | 5/2013 | DiPerna |
| 8,449,523 B2 | 5/2013 | Brukalo et al. |
| 8,486,005 B2 | 7/2013 | Yodfat et al. |
| 8,502,662 B2 | 8/2013 | Pohlman et al. |
| 8,504,179 B2 | 8/2013 | Blomquist |
| 8,768,717 B2 | 7/2014 | Blomquist |
| 8,858,526 B2 | 10/2014 | Blomquist |
| 2002/0040208 A1 | 4/2002 | Flaherty et al. |
| 2002/0072733 A1 | 6/2002 | Flaherty |
| 2003/0060765 A1 | 3/2003 | Campbell et al. |
| 2003/0208113 A1 | 11/2003 | Mault et al. |
| 2003/0212364 A1 | 11/2003 | Mann et al. |
| 2004/0054263 A1 | 3/2004 | Moerman et al. |
| 2004/0073095 A1 | 4/2004 | Causey et al. |
| 2004/0122353 A1 | 6/2004 | Shahmirian et al. |
| 2004/0260233 A1 | 12/2004 | Garibotto et al. |
| 2005/0137530 A1 | 6/2005 | Campbell et al. |
| 2005/0171512 A1 | 8/2005 | Flaherty |
| 2005/0171513 A1 | 8/2005 | Mann et al. |
| 2005/0177395 A1 | 8/2005 | Blomquist |
| 2005/0246416 A1 | 11/2005 | Blomquist |
| 2006/0250260 A1* | 11/2006 | Albert ................ G06F 19/3418 340/628 |
| 2007/0016170 A1 | 1/2007 | Kovelman |
| 2007/0156033 A1 | 7/2007 | Causey, III et al. |
| 2007/0219480 A1 | 9/2007 | Kamen et al. |
| 2007/0219496 A1 | 9/2007 | Kamen et al. |
| 2007/0219597 A1 | 9/2007 | Kamen et al. |
| 2007/0228071 A1 | 10/2007 | Kamen et al. |
| 2007/0251835 A1 | 11/2007 | Mehta et al. |
| 2007/0253021 A1 | 11/2007 | Mehta et al. |
| 2007/0253380 A1 | 11/2007 | Jollota et al. |
| 2007/0254593 A1 | 11/2007 | Jollota et al. |
| 2007/0255116 A1 | 11/2007 | Mehta et al. |
| 2007/0255125 A1 | 11/2007 | Moberg et al. |
| 2007/0255126 A1 | 11/2007 | Moberg et al. |
| 2007/0255348 A1 | 11/2007 | Holtzclaw |
| 2007/0258395 A1 | 11/2007 | Jollota et al. |
| 2008/0033357 A1 | 2/2008 | Mann et al. |
| 2008/0033360 A1 | 2/2008 | Evans et al. |
| 2008/0033749 A1 | 2/2008 | Blomquist |
| 2008/0065016 A1 | 3/2008 | Blomquist et al. |
| 2008/0076969 A1 | 3/2008 | Kraft et al. |
| 2008/0125700 A1 | 5/2008 | Moberg et al. |
| 2008/0126969 A1 | 5/2008 | Blomquist |
| 2008/0147004 A1 | 6/2008 | Mann et al. |
| 2008/0147050 A1 | 6/2008 | Mann et al. |
| 2008/0183054 A1* | 7/2008 | Kroeger ............. G06F 19/3418 600/301 |
| 2008/0306434 A1 | 12/2008 | Dobbles et al. |
| 2008/0306444 A1 | 12/2008 | Brister et al. |
| 2009/0085768 A1 | 4/2009 | Patel et al. |
| 2009/0088731 A1 | 4/2009 | Campbell et al. |
| 2009/0112626 A1 | 4/2009 | Talbot et al. |
| 2009/0270833 A1 | 10/2009 | DeBelser et al. |
| 2010/0198183 A1 | 8/2010 | Lanigan et al. |
| 2010/0274218 A1 | 10/2010 | Yodfat et al. |
| 2010/0280442 A1 | 11/2010 | Shahmirian et al. |
| 2011/0006876 A1 | 1/2011 | Moberg et al. |
| 2011/0009725 A1 | 1/2011 | Hill et al. |
| 2011/0009813 A1 | 1/2011 | Rankers |
| 2011/0021898 A1 | 1/2011 | Wei et al. |
| 2011/0071464 A1 | 3/2011 | Palerm |
| 2011/0071765 A1 | 3/2011 | Yodfat et al. |
| 2011/0098637 A1 | 4/2011 | Hill |
| 2011/0098638 A1 | 4/2011 | Chawla et al. |
| 2011/0098674 A1 | 4/2011 | Vicente et al. |
| 2011/0105979 A1 | 5/2011 | Schlaeper et al. |
| 2011/0126188 A1 | 5/2011 | Bernstein et al. |
| 2011/0144586 A1 | 6/2011 | Michaud et al. |
| 2011/0149759 A1 | 6/2011 | Jollota |
| 2011/0152970 A1 | 6/2011 | Jollota et al. |
| 2011/0163881 A1 | 7/2011 | Halff et al. |
| 2011/0178462 A1 | 7/2011 | Moberg et al. |
| 2011/0190694 A1 | 8/2011 | Lanier, Jr. et al. |
| 2011/0256024 A1 | 10/2011 | Cole et al. |
| 2011/0266999 A1 | 11/2011 | Yodfat et al. |
| 2012/0095315 A1 | 4/2012 | Tenbarge et al. |
| 2012/0172802 A1 | 7/2012 | Blomquist |
| 2012/0185267 A1 | 7/2012 | Kamen et al. |
| 2012/0191052 A1 | 7/2012 | Rao |
| 2012/0232520 A1 | 9/2012 | Sloan et al. |
| 2012/0277667 A1 | 11/2012 | Yodat et al. |
| 2013/0012878 A1 | 1/2013 | Blomquist |
| 2013/0012879 A1 | 1/2013 | DeBelser et al. |
| 2013/0012880 A1 | 1/2013 | Blomquist |
| 2013/0015980 A1 | 1/2013 | Evans et al. |
| 2013/0018315 A1 | 1/2013 | Blomquist |
| 2013/0131630 A1 | 5/2013 | Blomquist |
| 2013/0162426 A1* | 6/2013 | Wiesner ............... A61B 5/746 340/539.1 |
| 2014/0012511 A1 | 1/2014 | Mensinger et al. |
| 2014/0054883 A1 | 2/2014 | Lanigan et al. |
| 2014/0094744 A1 | 4/2014 | Blomquist |
| 2014/0094764 A1 | 4/2014 | Blomquist |
| 2014/0095485 A1 | 4/2014 | Blomquist |
| 2014/0095499 A1 | 4/2014 | Blomquist |
| 2014/0276571 A1 | 9/2014 | Ludolph |
| 2015/0126117 A1* | 5/2015 | Wong ................ H04W 52/0229 455/41.2 |
| 2015/0248823 A1* | 9/2015 | Jinno ..................... G06Q 30/06 340/692 |

* cited by examiner

SYSTEM AND METHOD FOR DETECTING AND TRANSMITTING MEDICAL DEVICE ALARM WITH A SMARTPHONE APPLICATION

RELATED APPLICATION

The present invention claims the benefit of U.S. Provisional Application No. 61/875,979 filed Sep. 10, 2013, which is incorporated herein by reference in its entirety.

FIELD OF THE INVENTION

The present invention relates to transmitting alerts or alarms from medical devices and, more particularly, to a smartphone application capable of detecting and relaying an alarm from a medical device.

BACKGROUND

Many medical devices include monitoring systems that monitor various conditions and provide alarms in response to various predetermined events. Such monitored conditions and events can, for example, pertain to the medical device itself, such as battery level, or to the patient being treated with the medical device, including a number of physiological parameters or conditions of the patient.

With the increase in home and self medical care, these alarms must be monitored by patients themselves rather than trained medical personnel. In the case of a child or other individual needing another to oversee medical assistance, such alarms need to be monitored by a caregiver such as a parent or other adult. In such situations, monitoring of medical device alarms at night while members of the household are asleep can be particularly challenging given that the caregiver responsible for the patient will generally be sleeping in a room separate from the patient and associated medical device and therefore may not hear an alarm or alert from the medical device.

Therefore, there is a need for a system and a method that aids in alerting a parent or other caregiver to a medical device alarm condition of a child or other individual whose treatment is the responsibility of the parent or other caregiver when the medical device is in a remote location.

SUMMARY OF THE INVENTION

A system and method provide for relaying a medical device alarm to a remote location without having a device electrically interconnected with the medical device. The system includes a relay device having software that can store specific alarm patterns or sequences for one or more alarms for a medical device. The relay device can then detect one or more of an audible, visual or tactile alarm from the medical device through corresponding devices or sensors in the relay device. Upon detection of an alarm, the relay device can transmit information pertaining to the alarm to a remote device to notify a user of the remote device of the medical device alarm.

In one embodiment, a smartphone or other device can utilize a software application that permits the smartphone to function as a relay device to relay medical device alarms. The application can provide for storing information pertaining to alarms for a specific medical device or type of medical device in the smartphone memory. In some embodiments, the alarms can be preprogrammed into the application or downloaded through the application. In other embodiments, the application can learn alarm sequences or patterns by being activated when test alarms are issued. In use, the smartphone can be placed adjacent the medical device with the relay application active. Upon occurrence of an alarm, the smartphone can detect the alarm through, for example, the sound, vibrations, light, etc. pattern of the alarm and recognize the alarm if stored in the application memory. The smartphone can then transmit the alarm and/or information pertaining to the alarm to a caregiver device, such as a smartphone, thus alerting a caregiver to an alarm occurring on a remotely located medical device.

Certain embodiments are described further in the following description, examples, claims, and drawings. These embodiments will become more apparent from the following detailed description when taken in conjunction with the accompanying exemplary drawings.

DETAILED DESCRIPTION

Figure 1:
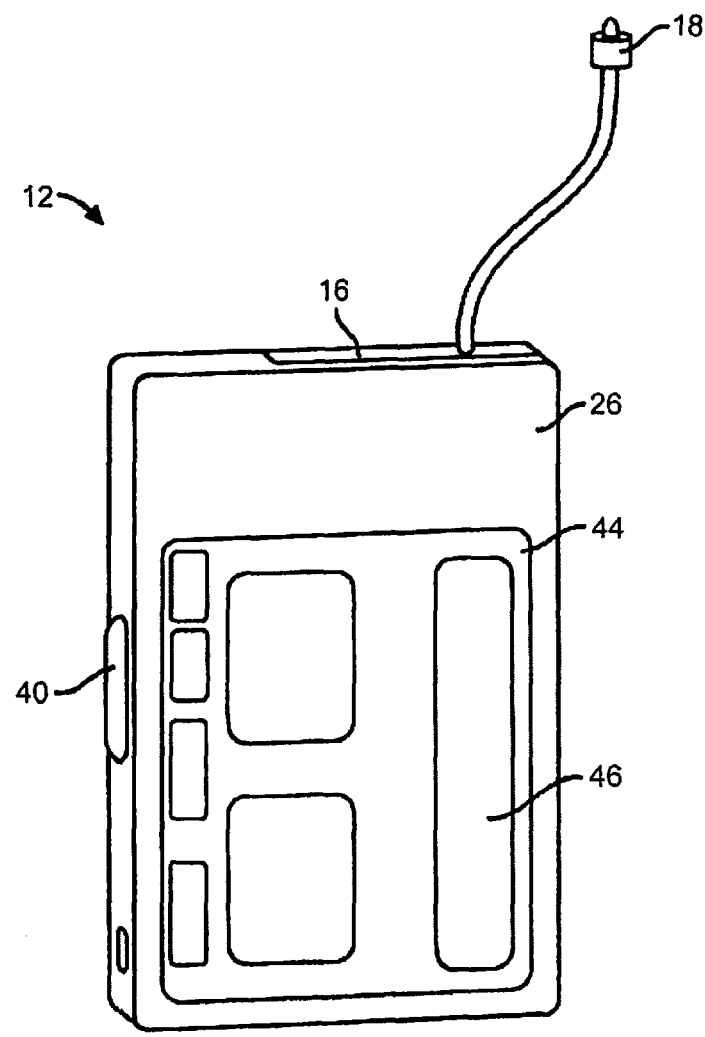
FIG. 1 is a medical device that can be utilized with embodiments of the present invention.

FIG. 1 depicts an embodiment of a medical device that can be used with embodiments of the present invention. In this embodiment, medical device is configured as a pump 12 such as an infusion pump that can include an internal pumping or delivery mechanism and reservoir for delivering medicament to a patient and an output/display 44. The type of output/display 44 may vary as may be useful for a particular application. The type of visual output/display may include LCD displays, LED displays, plasma displays, graphene-based displays, OLED displays and the like. The output/display 44 may include an interactive or touch sensitive screen 46 having an input device such as, for example, a touch screen comprising a capacitive screen or a resistive screen. The pump 12 may additionally include a keyboard, microphone, or other input device known in the art for data entry, which may be separate from the display. The pump 12 may also include a capability to operatively couple to a secondary display device such as a remote display, a remote control device, a laptop computer, personal computer, tablet computer, mobile communication device such as a smartphone or personal digital assistant (PDA) or the like.

In one embodiment, medical device can be a portable insulin pump configured to deliver insulin to a patient. Further details regarding such pump devices can be found in U.S. Patent Application No. 2011/0144586, which is incorporated herein by reference in its entirety. In other embodiments, medical device can be an infusion pump configured to deliver one or more additional or other medicaments to a patient. In a further embodiment, the medical device can be a glucose meter such as a continuous glucose monitor. Further detail regarding such systems and definitions of related terms can be found in, e.g., U.S. Pat. Nos. 8,311,749, 7,711,402 and 7,497,827, each of which is hereby incorporated by reference herein in its entirety. In other embodiments, the medical device can monitor other physiological parameters of a patient.

Figure 2:
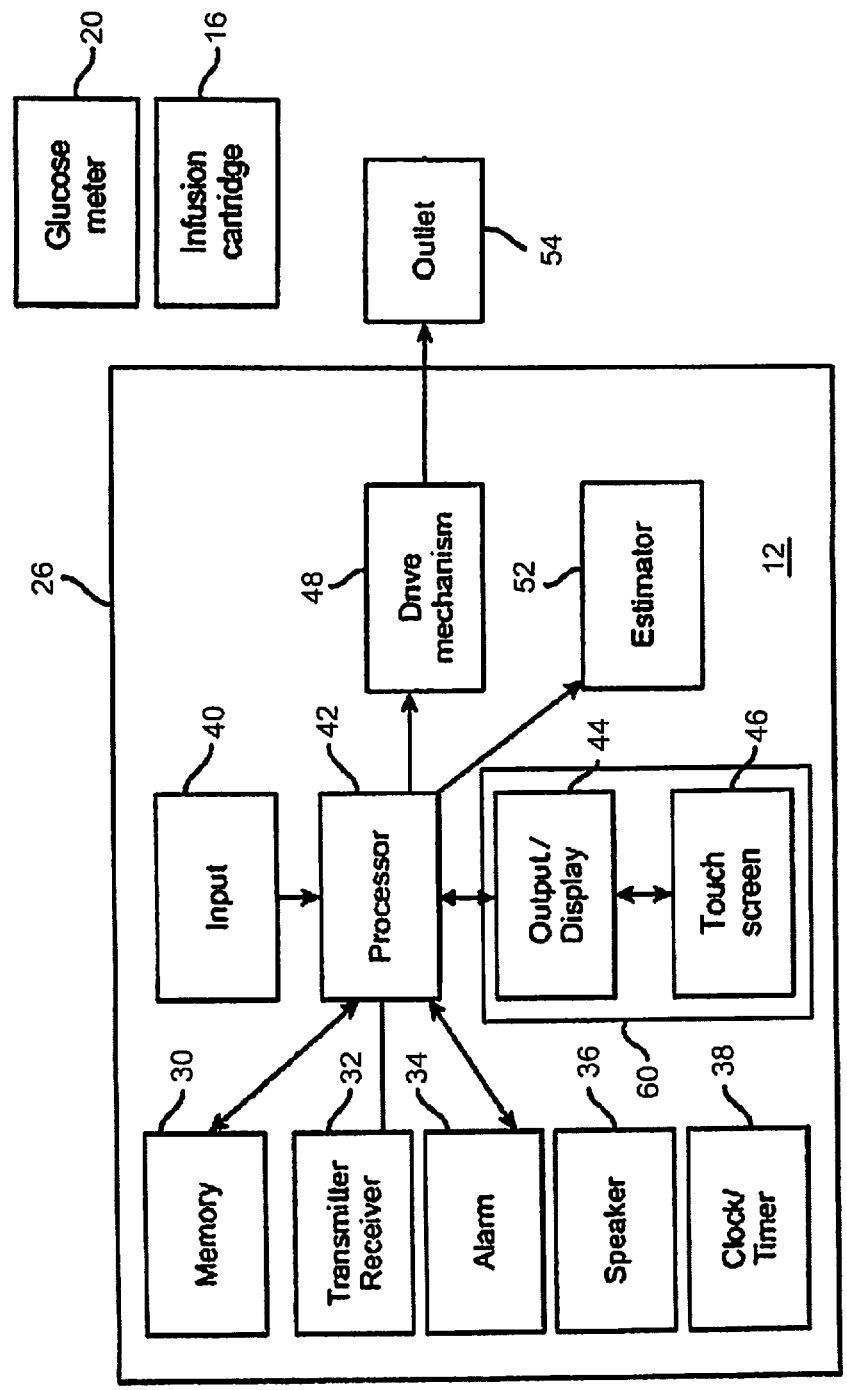
FIG. 2 is a block diagram representing a medical device that can be used with embodiments of the present invention.

FIG. 2 illustrates a block diagram of some of the features that can be used with embodiments of the present invention, including features that may be incorporated within the housing 26 of a medical device such as a pump 12. The pump 12 can include a processor 42 that controls the overall functions of the device. The infusion pump 12 may also include, e.g., a memory device 30, a communications device such as a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface as shown in FIG. 2 is a graphical user interface (GUI) 60 having a touch sensitive screen 46 with input capability. In some embodiments, the processor 42 may communicate with another processor within the pump 12 and/or one or more processors of other devices, for example, a continuous glucose monitor (CGM), display device, smartphone, etc. through the transmitter/receiver. The processor 42 may also include programming that may allow the processor to receive signals and/or other data from an input device, such as a sensor that may sense pressure, temperature or other parameters.

Figure 3:
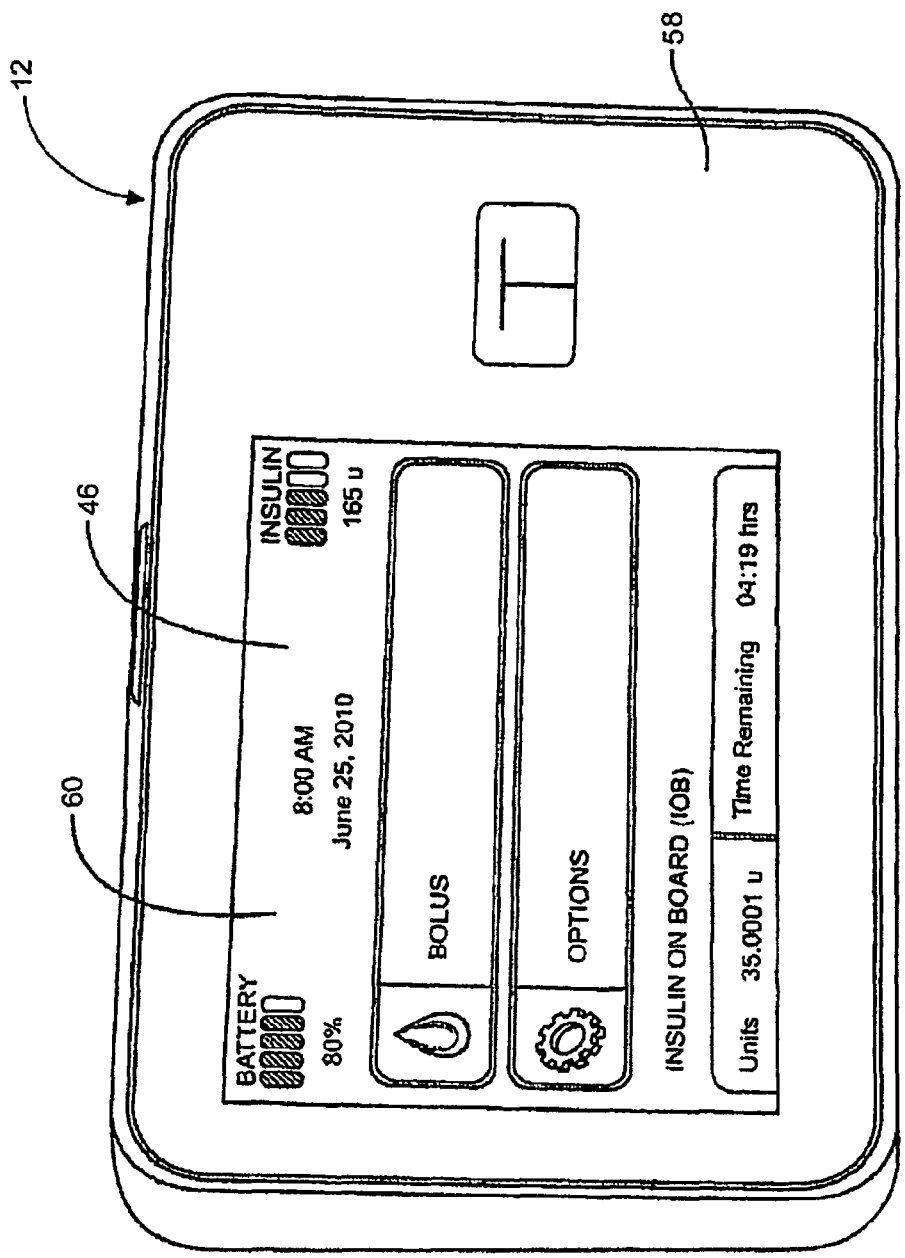
FIG. 3 depicts a screen shot of a home screen page of a graphical user interface of a medical device that can be used with embodiments of the present invention.

Referring to FIG. 3, a front view of pump 12 is depicted. The pump 12 may include a user interface, such as, for example, a user-friendly GUI 60 on a front surface 58 or other location of pump 12. The GUI 60 may include a touch-sensitive screen 46 that may be configured for displaying data, facilitating data and/or command entry, providing visual tutorials, as well as other interface features that may be useful to the patient operating the pump 12. The GUI can also present alarms or alerts to the user.

Alarms or alerts can be indicated by the medical device through one or more of a visual indication, auditory indication, tactile indication, and the like. A variety of pre-programmed or user programmed alarms can be integrated into the medical device for at least assisting in alerting the user and/or preventing user error. For instance, the medical device may utilize the GUI to present important information to the user as to the status of the device (e.g., battery life, remaining medicament in a cartridge, occlusion in a fluid line, etc.). The medical device can also alert the user for various reasons relating to physiological measurements of the user. For example, the medical device may warn the user when a physiological parameter of the user has reached a level that could be harmful to the user, such as, for example, a low or high blood glucose level. The medical device may warn the user, e.g., by changing one or more colors or text on a display screen of the medical device to alert the user. Alternatively, or in combination, the medical device may alert the user by sounding an alarm (e.g., a beeping noise or series of noises or a voice recorded alarm) or vibrating the device once or several times. In some embodiments, different types of alerts and alarms may have different characteristics, such as patterns, frequencies, volume/intensity levels, etc.

During periods where a caregiver such as a parent is remote from the patient and medical device, such alarms may go unnoticed and/or unaddressed, such as when a parent is sleeping in a separate room from a child patient. In such situations, wireless transmission of the alarm to a remotely located device of the caregiver can provide the caregiver with the alarm without having to be physically near the medical device. The caregiver device can be any device capable of receiving remote communications, such as, for example, a mobile phone, e.g., a smartphone, an electronic tablet or a laptop or desktop computer. The notification received by the caregiver device can be in any form, including, for example, a phone call, text message, email or instant message. The caregiver device could issue a warning configured as a voice recording or computer generated voice either automatically or when a phone call is answered, text message or email is opened, etc. Such a voice message warning, as well as any text warning, could be a general warning or a specific warning including, for example, the patient's name and the specific reason for the warning, such as a specified high or low blood glucose level of the patient.

In one embodiment, the alarm can be directly transmitted to the caregiver device from the medical device. Such transmission could be done wirelessly via, for example, Bluetooth®, cellular or Wi-Fi communications. The caregiver device could sense the transmission with, for example, a software application installed on the caregiver device, and alert the caregiver to the alarm via visual, audible or tactile means.

Figure 4:
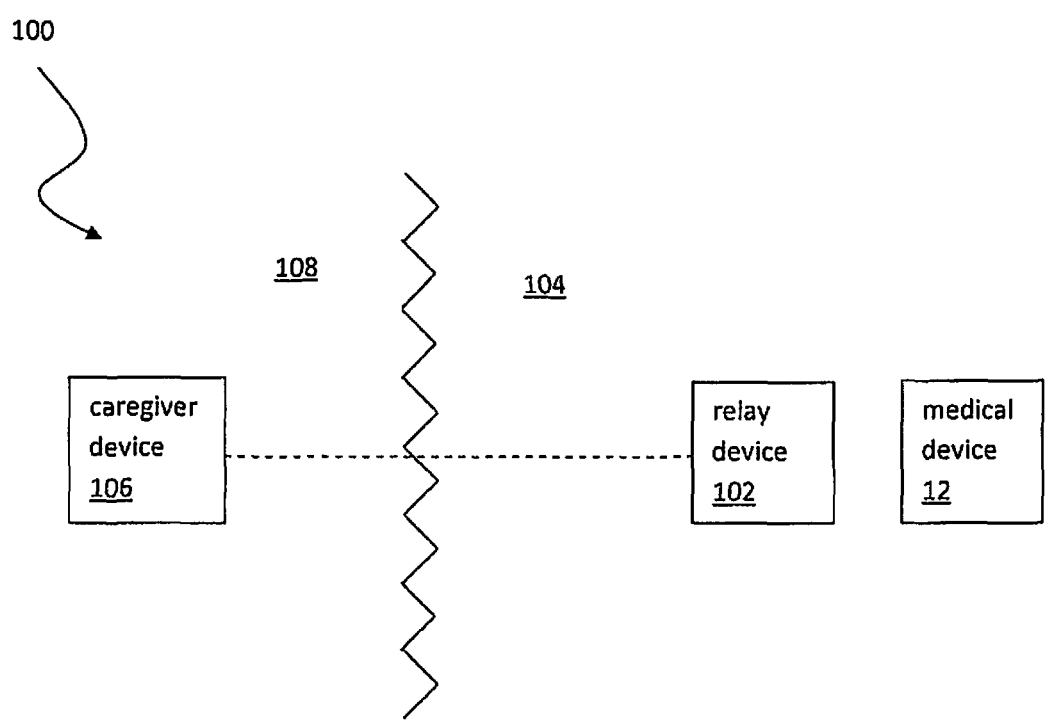
FIG. 4 is schematic representation of a system for relaying a medical device alarm according to an embodiment of the present invention.

However, many current medical devices do not include the circuitry or technology for direct wireless communication with mobile phones or computer networks in order to share information with others in real-time. As such, other embodiments of the invention employ an intermediary or relay device that can be located in proximity to the medical device and sense the alarm without being electronically integrated with or communicating with the medical device and wirelessly relay the alarm to the caregiver device. FIG. 4 depicts a schematic representation of such a system 100. Medical device 12 and relay device 102 are located near each other in a first location 104, but are not functionally linked for electronic communication with each other. The caregiver device 106 is located in a second location 108 that is remote from the first location 104. When an alarm or alert is issued by the medical device 12, the relay device 102 senses the alarm and wirelessly transmits the alarm to the caregiver device 106. The caregiver device 106 then provides the alarm directly to the caregiver via one or more of, for example, audible, visual or tactile means.

The relay device 102 can, for example, include a smartphone or electronic tablet or can be a dedicated device specifically configured to sense alarms and relay them to another device. In some embodiments, software installed on a smartphone or tablet as an application is specially designed to detect alarms of one or more types of medical devices. In various embodiments, the relay device 102 can detect audible alarms sounds, such as with a microphone or other audio sensor, vibration alarms, such as with an accelerometer or other tactile sensor, or light or visual alarms, such as with a camera or other light sensor. When an output from the medical device 12 is detected by the relay device 102, the device software can sense the specific characteristics of the output of the alarm and determine whether the output corresponds to one or more stored alarms and, if so, relay any of all alarms to which the output corresponds to the caregiver device 106. The alert sent to the caregiver device 106 can be in the form of a generalized alert or can identify a specific alarm or category of an alarm as having occurred. In some embodiments, the alert can also included a suggestion for addressing the alarm and/or the underlying cause of the alarm.

In some embodiments, relay device 102 can be preprogrammed with various alarm characteristics such as sequences and displays, vibration patterns, frequencies etc.

of one or more specific medical devices. In other embodiments, the relay device 102 can learn the alarms of a medical device. For example, a user or caregiver can cause the medical device to issue an alarm by, for example, initiating an alarm test sequence, while the relay device 102 is in a learn alarm mode. The relay device 102 then stores the specific alarm sequence, vibration pattern, etc. of the alarm. In some embodiments, the user can also enter other information pertaining to the alarm that can be stored with and associated with the alarm characteristics, such as a type of alarm or a specific notification to be sent to the caregiver device 106 upon detection of the alarm.

Alarm characteristics as referred to herein, can refer to any aspects of an alarm. For example, characteristics of an audible alarm can include a pattern or sequence of alarm sounds and pauses, volume of individual sounds, time length of individual sounds and sound frequencies. Characteristics of a tactile alarm can include, for example, a pattern or sequence of vibrations and pauses, intensity of individual vibrations and time length of individual vibrations. A visual alarm can include characteristics of, for example, a pattern or sequence of light emissions, color of light emissions, brightness of light emissions and time length of light emissions. Alarm characteristics can also be detected for a voice recording alarm and such characteristics can include the words used in the alarm as well as other audible characteristics of the voice recording as listed above.

Figure 5:
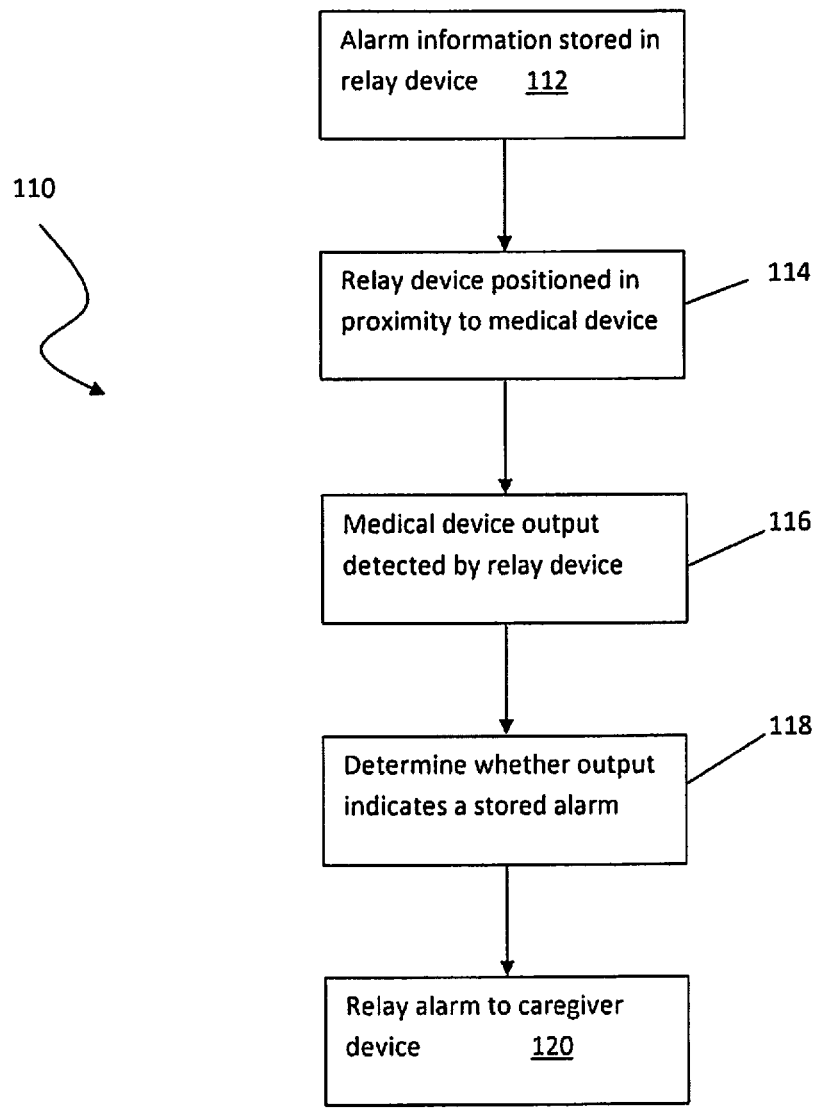
FIG. 5 is a flowchart of a method of relaying a medical device alarm according to an embodiment of the present invention.

FIG. 5 depicts a flowchart of a method 110 of relaying a medical device alarm according to an embodiment of the present invention. At step 112, a relay device such as relay device 102 stores one or more alarms of a specific type of medical device by, for example, being preprogrammed with alarm information or learning the alarm information. After the device has stored identification information for at least one alarm, it is placed in close proximity to the medical device at step 114. Close proximity, for example, can be as close as to be physically touching the medical device or as far as anywhere in the same room as the medical device or even in different rooms or buildings, depending on signal strength, physical environment, etc. At step 116, an output from the medical device is detected by the relay device. Output can, for example, be audible, visual or tactile output. At step 118, the relay device compares characteristics of the detected output to the one or more stored alarms to determine if the output corresponds to an alarm. If the output corresponds to an alarm, the relay device relays the alarm to a caregiver device, such as a smartphone, via wireless communication at step 120.

Although the invention is generally described herein with respect to a relay device that utilizes software to detect and recognize medical device alarms and relay those alarms to a caregiver device, it should be understood that in other embodiments of the invention the caregiver device itself can utilize such software. Thus, the caregiver device can directly detect output from a medical device, compare characteristics of the output to alarms stored in memory, and provide an alert on the caregiver device pertaining to the alarm, for example.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Also incorporated herein by reference in their entirety are commonly owned U.S. Pat. Nos. 8,287,495; 8,408,421 and 8,448,824; commonly owned U.S. Patent Publication Nos. 2009/0287180; 2010/0008795; 2010/0071446; 2010/0218586; 2012/0123230; 2013/0053816; 2013/0159456; 2013/0306191; 2013/0324928; 2013/0332874; 2013/0283196; 2013/0331790; 2013/0331778; and commonly owned U.S. patent application Ser. Nos. 13/800,387; Ser. No. 13/800,453; Ser. No. 13/800,595; Ser. No. 13/827,383; Ser. No. 13/829,115; Ser. No. 13/832,531; Ser. No. 13/832,841; Ser. No. 13/837,661; Ser. No. 13/837,777; Ser. No. 13/838,084; Ser. No. 13/841,432; Ser. No. 13/842,005; Ser. No. 13/842,990 and Ser. No. 13/923,556; and commonly owned U.S. Provisional Application Ser. Nos. 61/874,428, 61/911,576, 61/920,902, 61/920,914, 61/920,923, 61/920,932; 61/920,940; 61/990,501; and 62/030,933.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519; 6,641,533; 6,554,798; 6,551,276; 6,295,506; and 5,665,065.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. An apparatus for relaying one or more medical device alarms to a remote location, comprising:
    memory configured to store information relating to one or more alarms of a medical device;
    an input device configured to sense output from the medical device outside of any electronic communication network;
    a communications device; and
    a processor communicatively coupled with the memory, input device and communications device, the processor configured to:
        detect output from the medical device as sensed by the input device with the processor not being in an electronic communications network with the medical device;

compare the detected output to the information relating to the one or more alarms of the medical device stored in the memory to determine if the output corresponds to one or more of the alarms; and directly transmit via the communications device any or all of the one or more alarms to a separate device of an individual caregiver.

2. The apparatus of claim 1, wherein the output is sound.

3. The apparatus of claim 2, wherein the input device is a microphone.

4. The apparatus of claim 1, wherein the output is one or more vibrations.

5. The apparatus of claim 4, wherein the input device is an accelerometer.

6. The apparatus of claim 1, wherein the output is light.

7. The apparatus of claim 6, wherein the input device is a camera.

8. The apparatus of claim 1, wherein information relating to one or more alarms of a medical device includes a specific pattern of one or more alarms.

9. The apparatus of claim 1, wherein the processor is further configured to operate in a learning mode in which output detected by the input device is stored in memory for later comparison with subsequently detected output.

10. The apparatus of claim 1, wherein, if the output corresponds to one or more alarms, the processor further is configured to determine a reason why the one or more alarms occurred and to transmit to a separate device information relating to the reason.

11. An apparatus for relaying one or more medical device alarms to a remote location, comprising:

memory configured to store information relating to one or more alarms of a medical device;

an audio sensor for sensing output from the medical device outside of any electronic communications network;

a transmitter for communicating one or more medical device alarms to a separate device; and a processor communicatively coupled with the memory, the audio sensor for sensing output and the transmitter for communicating medical device alarms, the processor configured to:

compare output from the medical device as sensed by the audio sensor to the information relating to the one or more alarms of the medical device stored in memory to determine if the output corresponds to one or more of the alarms; and directly transmit via the transmitter any or all of said one or more alarms to a separate device of an individual caregiver.

12. The apparatus of claim 11, wherein the output is sound.

13. The apparatus of claim 11, wherein the output is one or more vibrations.

14. The apparatus of claim 11, wherein the output is light.

15. The apparatus of claim 11, wherein information relating to one or more alarms of a medical device includes a pattern of one or more alarms.

16. The apparatus of claim 11, wherein the processor is further configured to operate in a learning mode in which output detected by the audio sensor for sensing output from the medical device is stored in memory for later comparison with subsequently detected output.

17. The apparatus of claim 11, wherein, if the output corresponds to one or more alarms, the processor further is configured to determine a reason why the one or more alarms occurred and to transmit to the separate device information relating to the reason.

18. A system for relaying one or more medical device alarms to a remote location, comprising:

a medical device; and a relay device that is not in an electronic communications network with the medical device, the relay device including:

memory configured to store information relating to one or more alarms of the medical device;

an input device configured to sense output from the medical device;

a communications device; and a processor communicatively coupled with the memory, input device and communications device, the processor configured to:

detect output from the medical device as sensed by the input device without receiving an electronic communication containing the output transmitted over an electronic communications network;

compare the detected output to the information relating to the one or more alarms of the medical device stored in the memory to determine if the output corresponds to one or more of the alarms; and directly transmit via the communications device any or all of said one or more alarms to a separate device of an individual caregiver.

19. The system of claim 18, wherein the input device senses at least one of the groups consisting of: a pattern of sounds emanating from the medical device, a pattern of vibrations emanating from the medical device and a pattern of light emanating from the medical device as the detected output.

20. The system of claim 18, wherein the processor is further configured to operate in a learning mode in which output detected by the input device is stored in memory for later comparison with subsequently detected output.

* * * * *